(12) United States Patent  
Wang et al.

(10) Patent No.: US 7,942,661 B2  
(45) Date of Patent: May 17, 2011

(54) BIFURCATED BALLOON FOLDING METHOD AND APPARATUS

(75) Inventors: Woon-Chung Wang, Columbia Heights, MN (US); Stephen Michael, New Hope, MN (US); Benjamin Arcand, Plymouth, MN (US); Stefen M. Pallazza, Maple Grove, MN (US); Zack Tegels, Otsego, MN (US); Karl A. Jagger, Deephaven, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 691 days.

(21) Appl. No.: 11/779,485

(22) Filed: Jul. 18, 2007

(65) Prior Publication Data

US 2009/0024088 A1    Jan. 22, 2009

(51) Int. Cl.
*B30B 7/04*       (2006.01)
*A61M 25/00*   (2006.01)

(52) U.S. Cl. ................... 425/324.1; 425/330; 425/343; 425/392; 425/394; 425/398

(58) Field of Classification Search ................ 425/343, 425/383, 392–393, 409, 450.1
See application file for complete search history.

(56) References Cited

U.S. PATENT DOCUMENTS

| | | |
|---|---|---|
| 4,906,244 A | 3/1990 | Pinchuk et al. |
| 4,935,190 A | 6/1990 | Tennerstedt |
| 5,037,392 A | 8/1991 | Hillstead |
| 5,053,007 A | 10/1991 | Euteneuer |
| 5,087,246 A | 2/1992 | Smith |
| 5,112,900 A | 5/1992 | Buddenhagen et al. |
| 5,147,302 A | 9/1992 | Euteneuer et al. |
| 5,163,989 A | 11/1992 | Campbell et al. |
| 5,209,799 A | 5/1993 | Vigil |
| 5,226,887 A | 7/1993 | Farr et al. |
| 5,306,246 A | 4/1994 | Sahatjian et al. |
| 5,318,587 A | 6/1994 | Davey |
| 5,320,634 A * | 6/1994 | Vigil et al. ............... 606/159 |
| 5,342,307 A | 8/1994 | Euteneuer et al. |
| 5,348,538 A | 9/1994 | Wang et al. |
| 5,350,361 A | 9/1994 | Tsukashima et al. |
| 5,403,340 A | 4/1995 | Wang et al. |
| 5,447,497 A | 9/1995 | Sogard et al. |
| 5,456,666 A | 10/1995 | Campbell et al. |
| 5,458,572 A | 10/1995 | Campbell et al. |
| 5,478,319 A | 12/1995 | Campbell et al. |
| 5,549,552 A | 8/1996 | Peters et al. |
| 5,550,180 A | 8/1996 | Elsik et al. |
| 5,556,383 A | 9/1996 | Wang et al. |

(Continued)

FOREIGN PATENT DOCUMENTS

EP          0 565 796          10/1993

(Continued)

*Primary Examiner* — Richard Crispino
*Assistant Examiner* — Martin Rogers
(74) *Attorney, Agent, or Firm* — Vidas, Arrett & Steinkraus, P.A.

(57) ABSTRACT

A balloon folding system specifically configured to reduce a side branch balloon of a bifurcated balloon catheter assembly includes a die that defines at least one chamber for receipt of the sidebranch balloon, and at least one pin sized to fit into the chamber and reduce the balloon to a substantially flattened state. The system also may include a housing for the reduction and folding of a primary branch balloon. The system is configurable to fold and reduce both branches simultaneously or separately.

11 Claims, 13 Drawing Sheets

U.S. PATENT DOCUMENTS

| | | | |
|---|---|---|---|
| 5,718,684 | A | 2/1998 | Gupta |
| 5,746,745 | A | 5/1998 | Abele et al. |
| 5,830,182 | A | 11/1998 | Wang et al. |
| 5,833,657 | A | 11/1998 | Reinhardt et al. |
| 5,882,334 | A | 3/1999 | Sepetka et al. |
| 5,951,941 | A | 9/1999 | Wang et al. |
| 6,013,055 | A | 1/2000 | Bampos et al. |
| 6,033,380 | A | 3/2000 | Butaric et al. |
| 6,071,285 | A | 6/2000 | Lashinski et al. |
| 6,126,652 | A | 10/2000 | McLeod et al. |
| 6,135,982 | A | 10/2000 | Campbell |
| 6,146,356 | A | 11/2000 | Wang et al. |
| 6,171,278 | B1 | 1/2001 | Wang et al. |
| 6,210,429 | B1 | 4/2001 | Vardi et al. |
| 6,328,925 | B1 | 12/2001 | Wang et al. |
| 6,387,117 | B1 * | 5/2002 | Arnold et al. ............... 623/1.1 |
| 6,406,457 | B1 | 6/2002 | Wang et al. |
| 6,481,262 | B2 * | 11/2002 | Ching et al. .................. 72/416 |
| 6,835,203 | B1 | 12/2004 | Vardi et al. |
| 6,946,092 | B1 | 9/2005 | Bertolino et al. |
| 7,220,275 | B2 | 5/2007 | Davidson et al. |
| 7,479,149 | B2 * | 1/2009 | Pallazza ...................... 606/191 |
| 2002/0163104 | A1 | 11/2002 | Motsenbocker et al. |
| 2002/0193873 | A1 | 12/2002 | Brucker et al. |
| 2003/0083687 | A1 | 5/2003 | Pallazza |
| 2003/0163157 | A1 * | 8/2003 | McMorrow et al. .......... 606/194 |
| 2003/0195606 | A1 | 10/2003 | Davidson et al. |
| 2004/0135281 | A1 | 7/2004 | Eidenschink |
| 2004/0138737 | A1 * | 7/2004 | Davidson et al. ............ 623/1.35 |
| 2004/0215227 | A1 * | 10/2004 | McMorrow et al. .......... 606/191 |
| 2004/0267352 | A1 | 12/2004 | Davidson et al. |
| 2005/0060027 | A1 | 3/2005 | Khenansho et al. |
| 2005/0102023 | A1 | 5/2005 | Yadin et al. |
| 2006/0015134 | A1 | 1/2006 | Trinidad |
| 2006/0036315 | A1 | 2/2006 | Yadin et al. |
| 2008/0048363 | A1 * | 2/2008 | Arcand ........................ 425/383 |

FOREIGN PATENT DOCUMENTS

| | | |
|---|---|---|
| WO | 94/23787 | 10/1994 |
| WO | 2005/118046 A1 | 12/2005 |

\* cited by examiner

BIFURCATED BALLOON FOLDING METHOD AND APPARATUS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to medical devices, such as catheter systems of all types, as well as their manufacture and assembly. Some embodiments are directed more specifically to bifurcated balloon catheters, and the methods and mechanisms directed to their manufacture and preparation for use.

2. Description of the Related Art

Atherosclerotic cardiovascular disease is common, and is caused by a narrowing of the arterial lining due to atherosclerotic plaques. Medical balloons are used in the body in the treatment of atherosclerotic cardiovascular disease and include dilatation devices, typically balloons for example, for dilating stenotic regions of an artery or other vessel, and/or for expanding prosthetic devices such as stents at a desired location therein.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels.

Some balloon catheters intended for use at vessel bifurcations may include auxiliary portions, such as an auxiliary inflation balloon. Such balloon catheters may be utilized to dilate the region of the lesion, such as in a balloon angioplasty procedure and/or are used to deliver and expand specialized stents that have dedicated side branch structures, wherein the auxiliary portions are used to achieve proper expansion of the stent's side branch structure. Some examples of bifurcated balloon catheters equipped with auxiliary or side branch balloons, and/or examples of stents having specialized side branch structures are found in: U.S. Pat. Nos. 6,210,429; 6,835,203; and 7,220,275, the entire contents of each being incorporated herein by reference.

Because it is typically necessary for balloon catheters of all types to traverse a tortuous anatomy as they are being advanced through one or more bodily vessels; it is desirable for the balloon to assume as low a profile, i.e. the outer diameter of the balloon, as possible. Considerable effort has been put forth in the development of dilatation balloons with a low profile by minimizing the dimensions of the core or the inner tube which extends through the balloon to its distal end, and by reducing the wall thickness of the balloon itself.

One way to achieve a low profile of the balloon is by folding the balloon to form a number of wings, which are then wrapped about the catheter shaft. Prior to use, the balloon is typically folded or wrapped about the balloon catheter to fit within and pass through a lumen of a guide catheter sized for insertion into the appropriate vessel or body lumen of the patient. When inflation fluid is applied to the deflated balloon, the balloon wings or flaps unwrap and the balloon inflates to a fully expanded condition.

Various techniques or balloon constructions have been employed to facilitate the folding of the balloon about the balloon catheter in a uniform manner upon evacuation and deflation of the balloon after use.

In the case of bifurcated balloon catheter systems employing an auxiliary or secondary balloon, the secondary balloon further increases the profile of the catheter system, thus affecting flexibility and deliverability of the system. The reduction and assembly of such bifurcated balloon catheter systems can also be significantly more time consuming than standard balloon catheters.

There remains a need for specialized preparation of suitable catheter systems in order to provide a compact, low profile delivery device, and which provides both the primary balloon and secondary balloon with a folded configuration that is efficiently achieved.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the present invention is directed to a system which is configured to reduced and fold the primary branch as well as the side branch portion of a fully assembled bifurcated balloon catheter in a single apparatus. The system can be configured to fold and reduce both branches simultaneously or separately as desired.

In embodiments wherein the side branch balloon is to be reduced separately from the primary balloon, the system will include a primary balloon folding apparatus and a secondary balloon reduction apparatus, wherein the secondary reduction apparatus receives the side branch balloon and shaft at an angle offset from the axis of orientation of the primary catheter branch.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
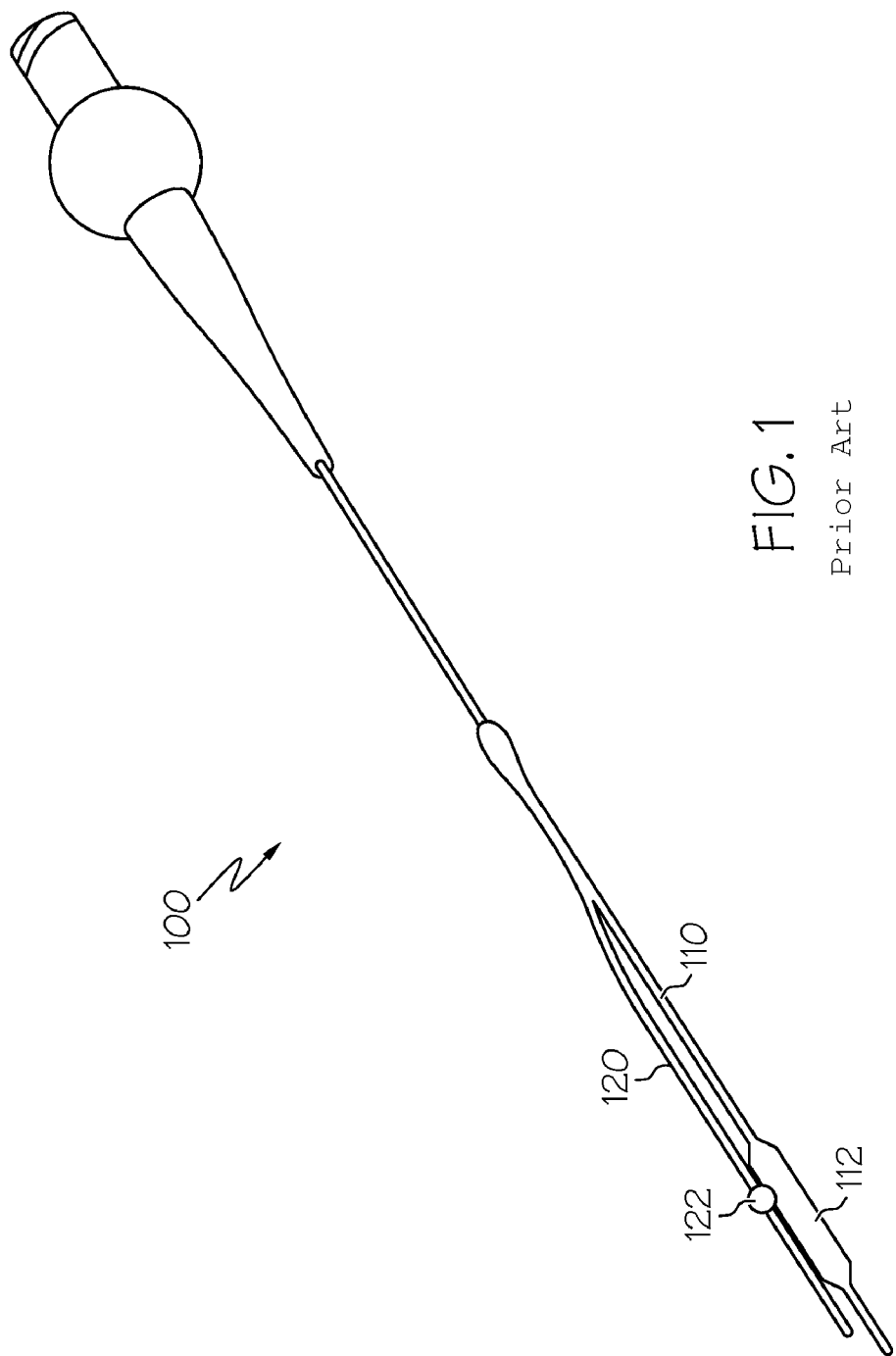
FIG. 1 shows a bifurcated balloon catheter suitable for use with the present invention.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

There are currently numerous types and configurations of bifurcated balloon catheters. One such style of catheter 100, such as is shown in FIG. 1, employs a primary branch catheter shaft 110 and a secondary or side branch catheter shaft 120. The primary branch includes a primary balloon 112, and the secondary branch includes a secondary or side branch balloon 122. While suitable for use in angioplasty procedures at vessel bifurcations, catheters of the type shown are also suitable for the delivery of bifurcated stents, particularly bifurcated stents having side branch 'petals' or other configurations wherein a side branch portion of the stent extends from but is integral with the primary stent body. Some examples of such stents and similar designs are described in U.S. Pat. Nos. 6,835,203; 7,220,275; 2003/0195606; 2004/0267352; 2005/0060027; 2005/0102023; and 2006/0036315, the entire contents of each being incorporated herein by reference.

When a catheter 100 is utilized to deliver such bifurcated stents, the primary balloon 112 is first expanded to deploy the primary stent body, which is followed by expansion of the side branch balloon 122 to deploy the side branch or petals of the stent into the lumen of the branch vessel at a vessel bifurcation.

In order to provide such catheters with a profile sufficient to accommodate advancement of the catheter through the tortuous confines of mammalian vasculature, both the primary balloon and the side branch balloon must be of the lowest profile possible, especially if the catheter is equipped with a stent. As such, embodiments of this invention are directed to systems and methods for folding and/or reducing both the primary balloon 112 and side branch balloon 122 of a bifurcated balloon catheter 100.

Figure 2:
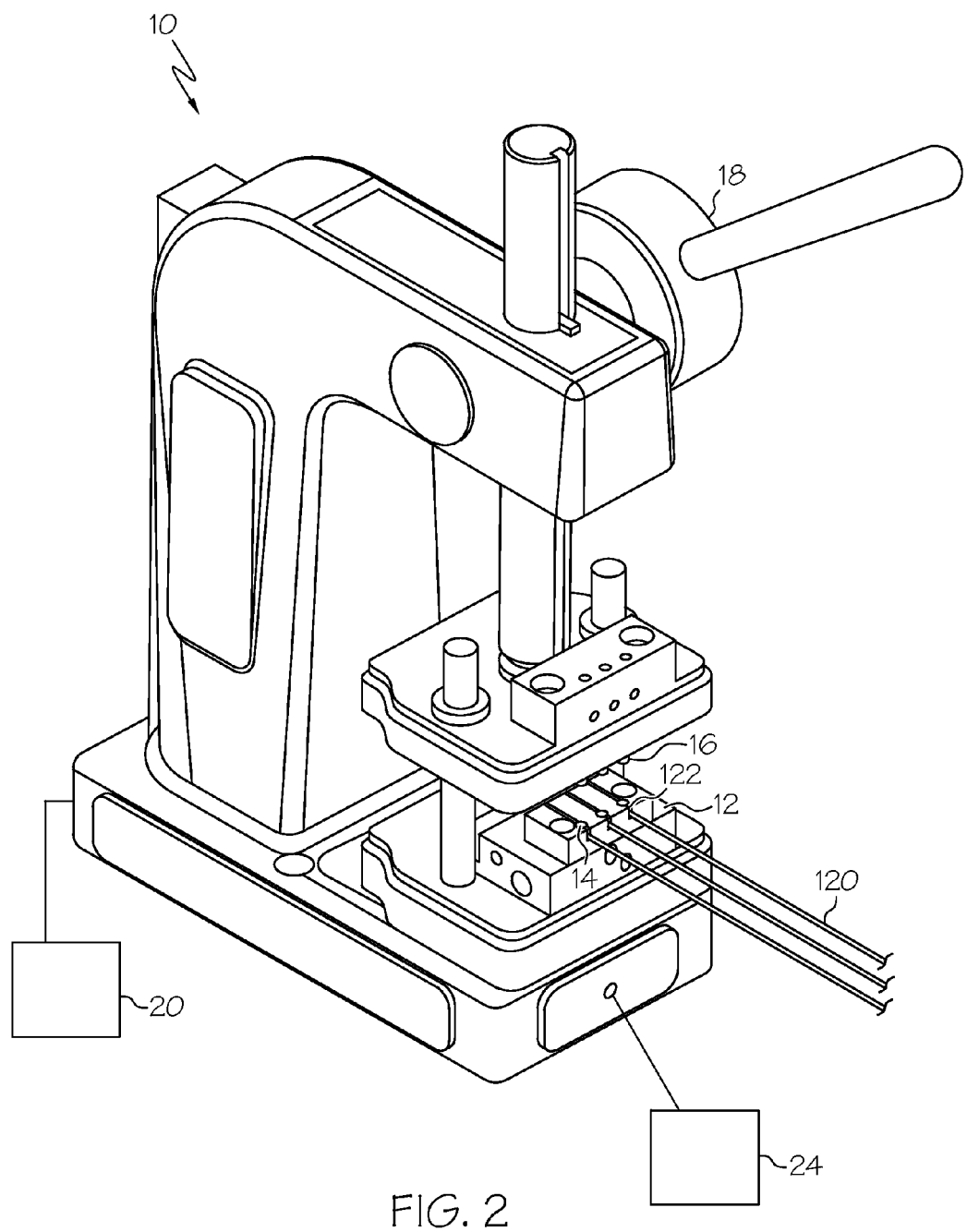
FIG. 2 is a perspective view of an embodiment of the invention comprising an apparatus for reducing the secondary or side branch portion of a bifurcated balloon catheter.

In the embodiment depicted in FIG. 2, a reducing apparatus 10 is shown which is configured to reduce the cross-sectional profile of a side branch balloon 122 of a bifurcated balloon catheter. In some embodiments the apparatus 10 is configured to receive the distal portion 121 of the side branch shaft 120 while it is still separate from the primary shaft 110, that is, before the catheter 100 is fully assembled. With such a configuration it will be recognized that the apparatus can be configured to receive a large number of side branch shafts 120 simultaneously. For example, in the embodiment shown in FIG. 2 the apparatus 10 comprises a die 12 that will accept up to three shafts 120. It will be recognized however that the die 12 can be easily configured to receive nearly any number of shaft desired.

Figure 3:
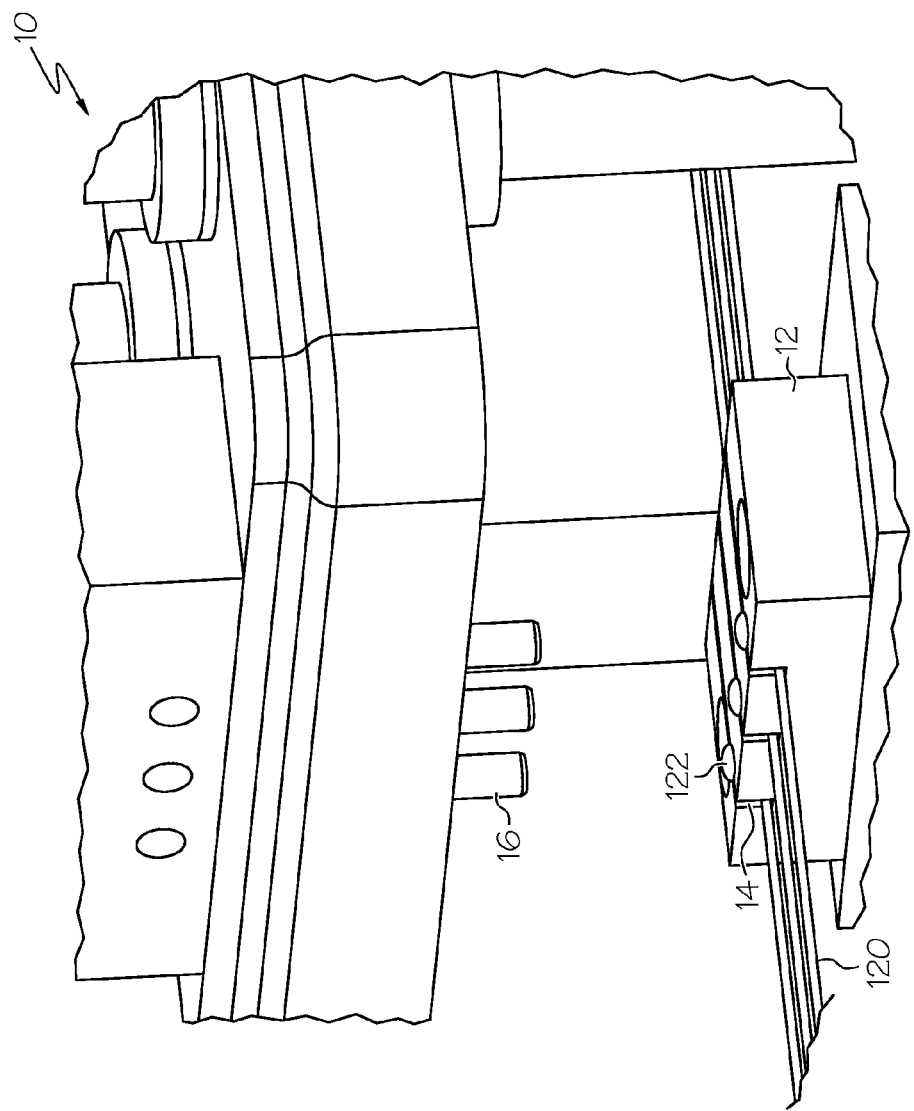
FIGS. 3 is a detailed view of a region of the apparatus shown in FIG. 2, including the die and pins for reducing the side branch balloon.

In the embodiment shown in FIGS. 2-7 the die 12 defines one or more reduction chambers 14, of which each is sized to receive the distal portion 121 of the side branch shaft 120, including the side branch balloon 122, such as in the manner illustrated in FIGS. 2-3.

In various embodiments the chamber 14 has an elongate shape configured to receive the side branch shaft 120 and a substantially cylindrical portion wherein the side branch balloon 122 is positioned. The shape of the chamber 14 can have any of a variety of shapes, sizes, and dimensions in order to accommodate any variety of side branch shafts and balloons. The chamber 14 can also be configured to accommodate any of a variety of shaft orientations relative to the balloon, including those wherein the proximal and distal portions of the shaft, relative to the balloon, have the same or different axes.

The portion of the chamber 14 in which the balloon is to be positioned is substantially cylindrical in shape, and has a diameter sufficient to accommodate the balloon 122 in an inflated state, wherein the balloon 122 is inflated to a pressure of about 10 psi to about 75 psi. A reduction pin 16 has a shape which substantially corresponds to the cylindrical portion of the chamber 14. The diameter of the pin 16 however, is only slightly less than that of the chamber 14 in order to allow the pin 16 to be inserted into the chamber 14 and push against the balloon 122, such as in the manner shown in FIG. 8.

Figure 8:
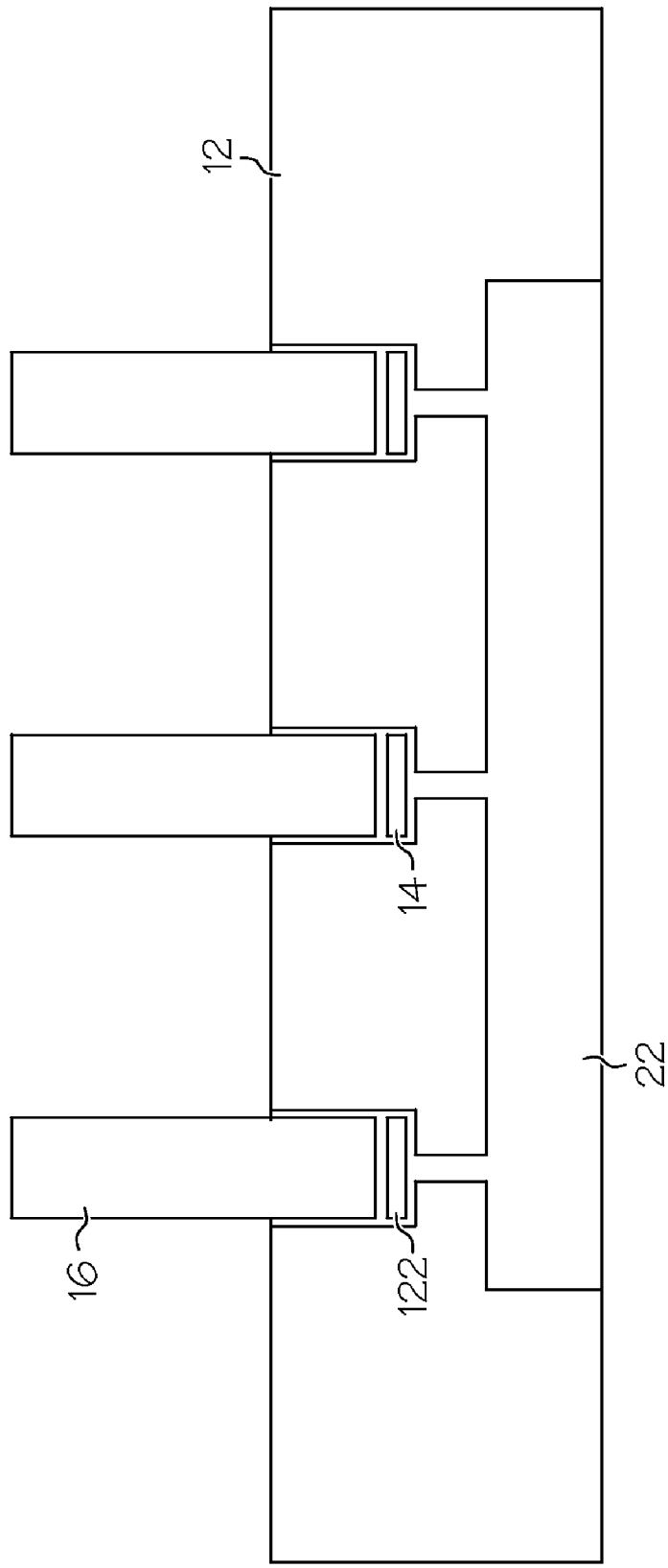
FIG. 8 is a cross-sectional view of a side branch balloon positioned within the reduction chamber of the die shown in FIGS. 2-7 in the reduced state.
Figure 9:
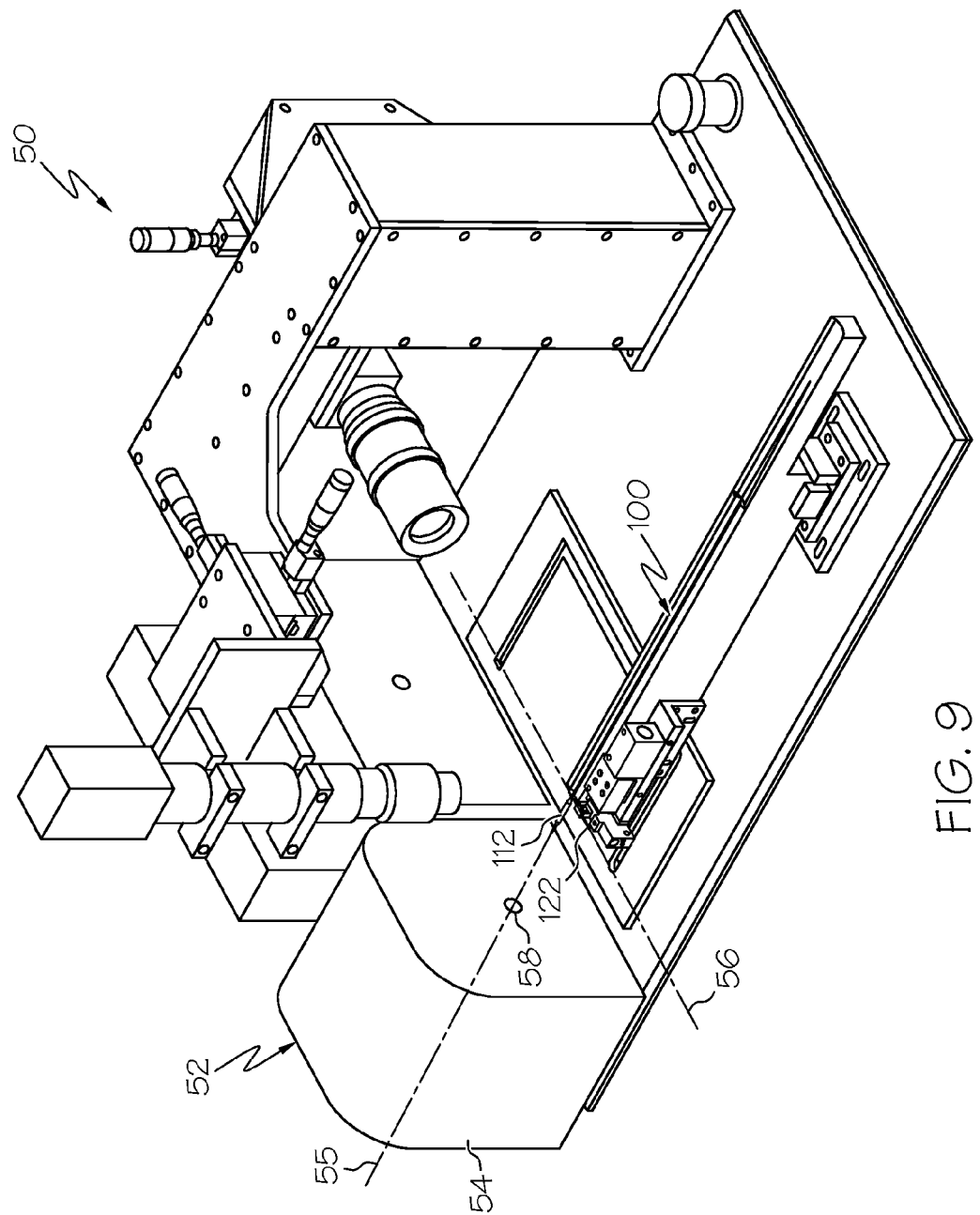
FIG. 9 is a perspective view of an embodiment of the invention comprising an system for reducing both the primary balloon and side branch balloon of a bifurcated balloon catheter.
Figure 10:
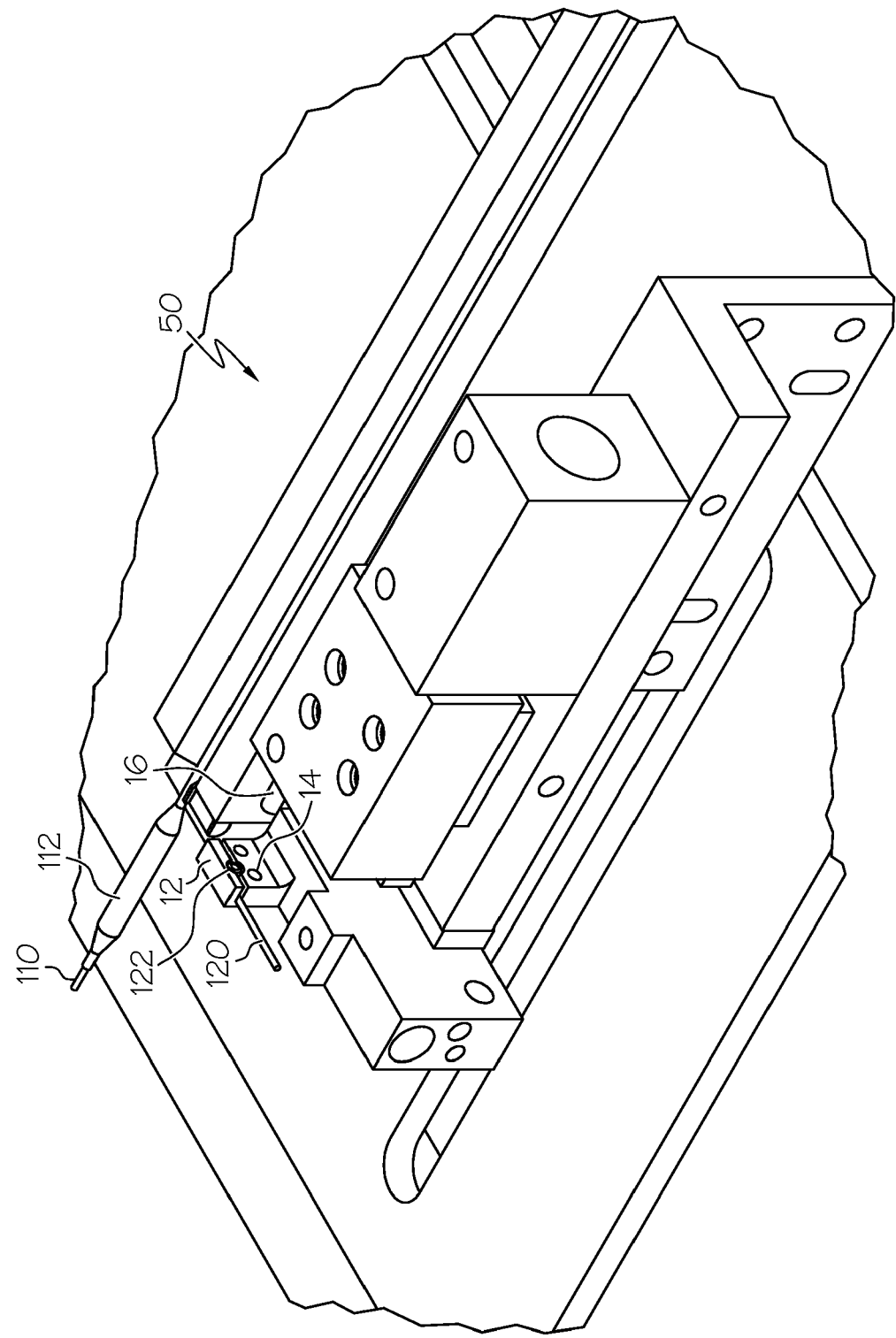
FIG. 10-12 are detailed views of the system shown in FIG. 9.

The pin or pins 16 are actuated from the open position shown in FIGS. 2-3 to the closed position in FIG. 8 by any of a variety of mechanisms. For example in FIG. 2 the apparatus 10 is provided with a lever 18 for direct mechanical actuation of the pins 16. Other actuation and control mechanisms include but are not limited to one or more hydraulic and/or pneumatics valves, pressure sources, etc.

It should further be noted that while in the embodiments shown in FIGS. 2-3 describe actuation of the pin(s) 16 into the reduction chamber 14, it should be understood that the apparatus can readily be configured such that the die 12 can be made to be actuated and moved onto the pin(s).

In some embodiments the apparatus includes a heat source 20 or other mechanism configured to heat the pin(s) 16 and/or the die 12 to a temperature of between about 35° C. to about 75° C.

Figure 4:
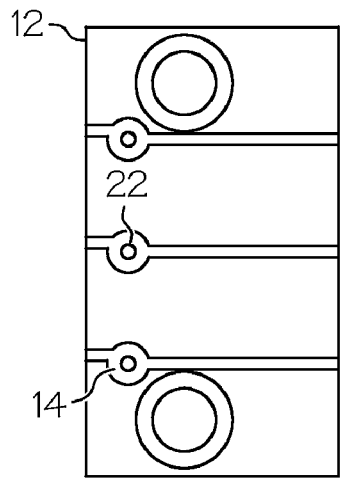
FIGS. 4-7 are alternative views of the die shown in FIG. 3.
Figure 5:
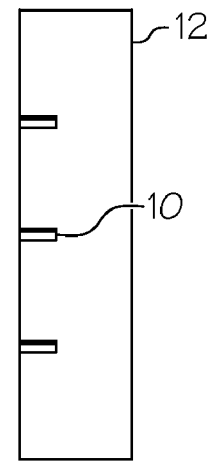
Figure 6:
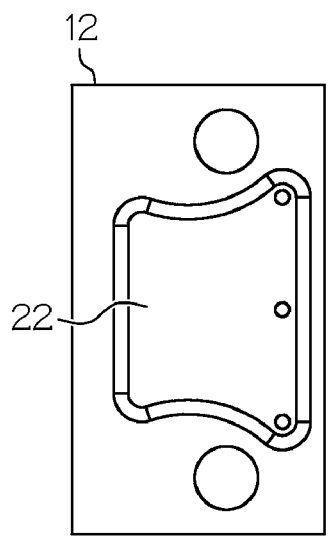
Figure 7:
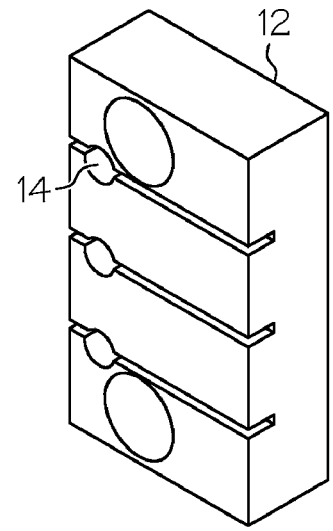

In some embodiments the die 12 further defines a vacuum chamber 22, which is in communication with the reduction chamber 14, such as is depicted in FIGS. 4 and 6. The vacuum chamber is in communication with a vacuum source 24 (illustrated in FIG. 2), such that when the reduction pin 16 is inserted into the chamber 14, the chamber 14 is evacuated to aid in the collapse of the side branch balloon 122 into the reduced state shown in FIG. 8. The application of vacuum to the side branch balloon 122 holds the balloon base flat against the die's bottom edge. This improves the consistency of the shape of the reduced balloon. In some embodiments the inside of the side branch balloon 122 is evacuated during the reduction step to further aid in the shape quality of the reduced balloon 122.

In some embodiments, an example of which is shown in FIGS. 9-12 a single chamber version of the die 12 is incorporated as part of a larger system 50, which is configured to reduce not only the side branch balloon 122 but the primary branch balloon 112 of a fully assembled bifurcated balloon catheter 100.

In the system shown in FIGS. 9-12, the die 12 and pin 16 have features and are arranged to interface in the same manner as previously described. In the embodiments depicted in FIGS. 9-12 however the system 50 further comprises a primary balloon folding and reducing apparatus 52. The apparatus 52 comprises a housing 54, which is disposed about a primary axis 55. The primary catheter branch 110 is inserted into the housing 54 along this axis. The reduction chamber 14 of the die 12 is disposed about a secondary axis 56.

Figure 11:
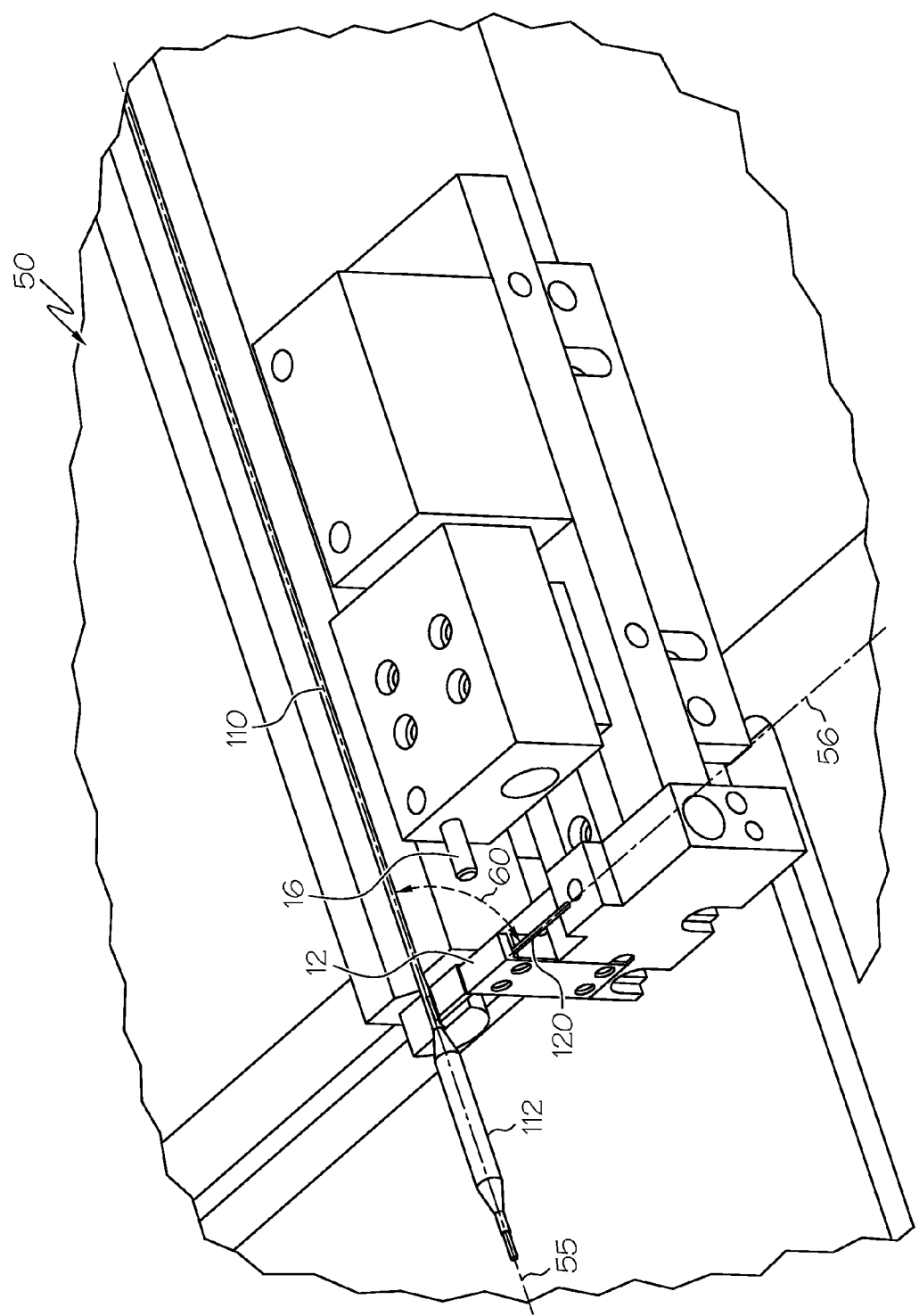
Figure 12:
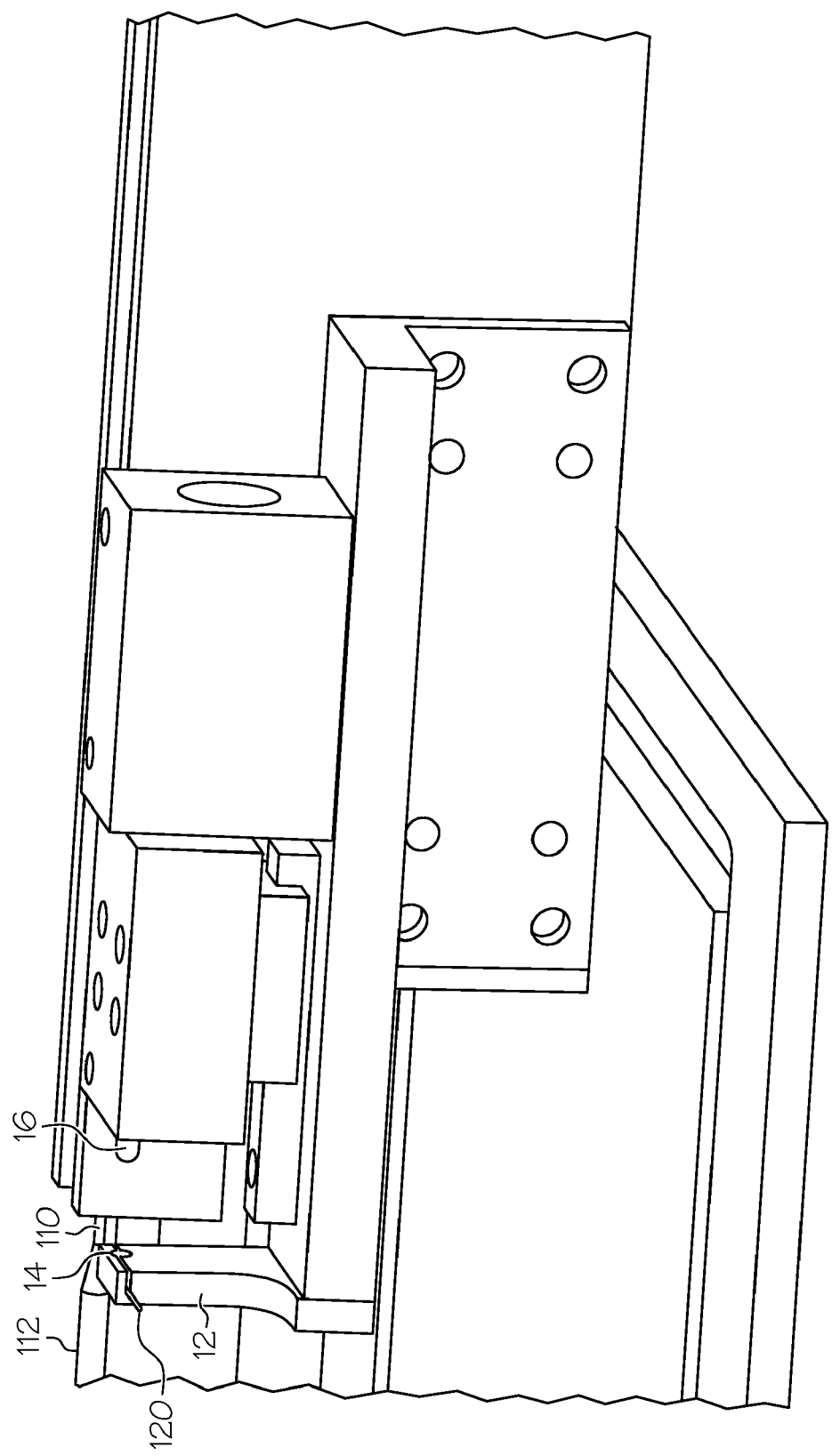

As is best shown in FIG. 11 the secondary axis 56 of the chamber 14 is offset from the primary axis 55 by an angle 60. Angle 60 can be an angle sufficient to allow the components of the system 50 to be assembled and arranged in a usable manner. In the embodiment presently depicted, angle 60 is about 90 degrees. While angle 60 can of course be modified, it should also be noted that the relative position of the secondary axis 56 can be varied in any or all three dimensions relative to the primary axis 55.

The housing 54 is configured to receive the primary branch 110 of a bifurcated balloon catheter 100 into the housing space 58. The internal configuration of the housing 54 may be any style of conventional balloon reducing (e.g. pleat forming, fold forming, wing forming, wrapping and/or diameter reducing) mechanism. Examples of folding apparatuses which the housing 54 is comprised of include but are not limited to the Balloon Folding Apparatuses shown and described in U.S. Published Applications 2003/0163157 and 2004/0215227 by McMorrow et al; the entire content of each being incorporated herein by reference.

In some embodiments, it may not be desirable to separately fold and reduce the primary balloon 112 and the side branch balloon 122. In such cases housing 54 can be configured to accept both shafts 110 and 120 of the catheter assembly at the same time.

Figure 13:
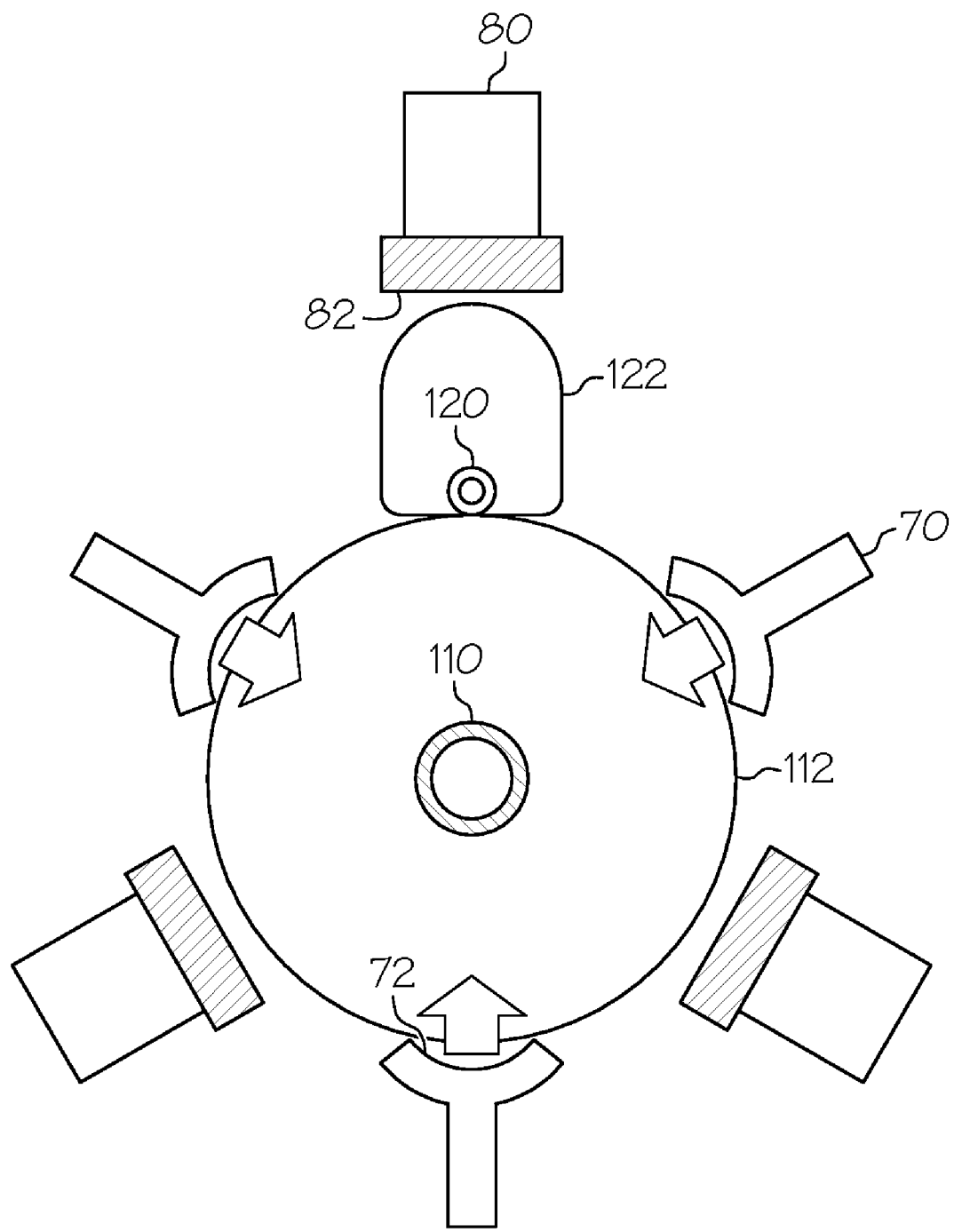
FIGS. 13-15 are cross-sectional views of the internal mechanisms of a balloon reducing and folding housing of the type shown in FIG. 9, configured to receive both the primary and secondary catheter shafts simultaneously.
Figure 14:
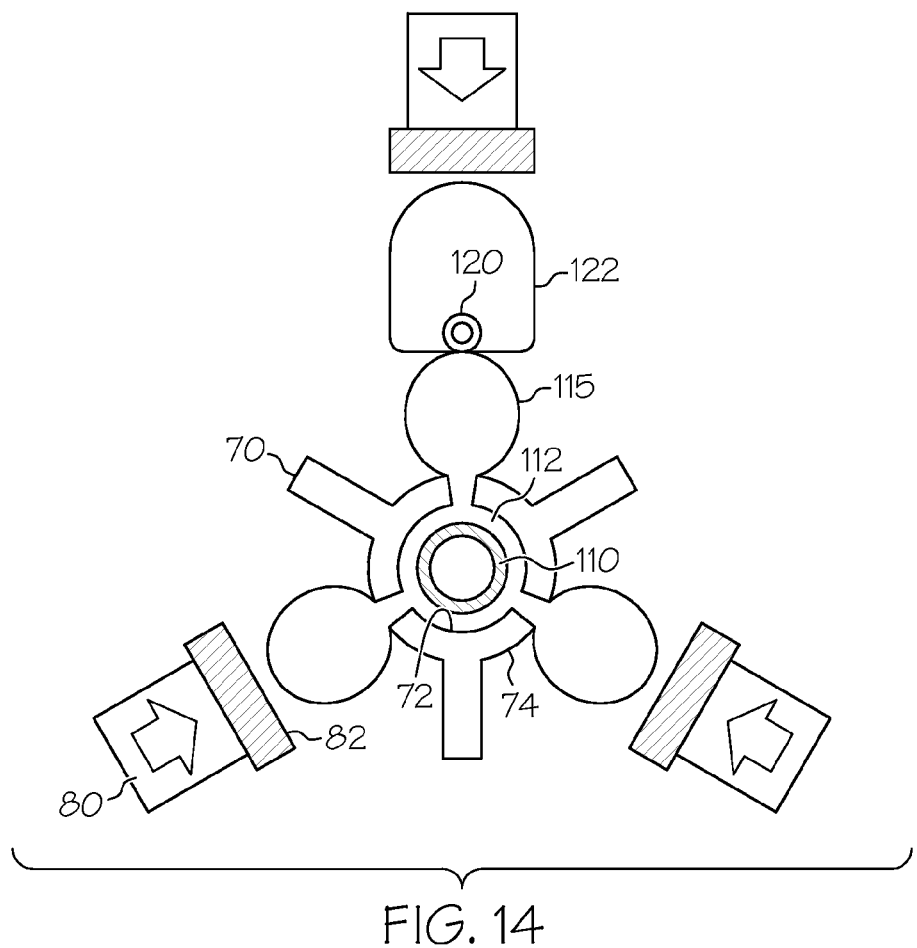
Figure 15:
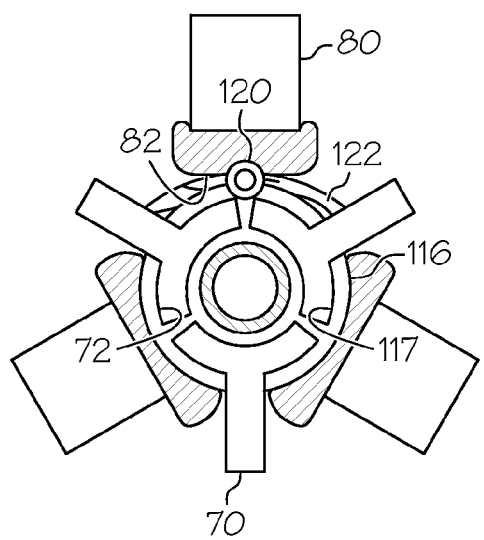

As is illustrated in FIGS. 13-15, the housing space 58 is defined by at least three pleat forming members 70 (a.k.a. first impinging members) and at least three compression members 80 (a.k.a. second impinging members) which are alternatingly arranged about the primary balloon 112 in a substantially concentric manner about the balloon 112. When the balloons 112 and 122 are inserted into the housing space 58 they are each inflated to an inflation pressure of about 10 psi to about 75 psi. Once the balloons are properly positioned and inflated to the desired pressure, such as in the manner shown in FIG. 13 the reduction and folding operations commence.

As illustrated in FIGS. 13 and 14, each of the pleat forming members 70 and each of the compression members 80 are moveable along a single axis (indicated by arrows) to provide the housing opening with an enlarged open diameter state sized to accept the inflated primary balloon and side branch balloon; and a reduced diameter state, wherein the balloons are first pleated and then folded, as depicted in FIGS. 14 and 15.

In operation, initially, only the pleat forming members 70 push inwardly against the primary balloon 112 to form at least three balloon lobes 115. The side branch balloon 122 will be positioned affectively on top of one of the primary balloon's lobes 115 following the pleat forming members 70 being actuated to the reduced state, such as in the manner shown in FIG. 14.

Each of the pleat forming members 70 comprise a pleat forming surface 72 which contact the primary balloon 112. Each surface 72 defines a portion of a curve, having an arc length within the range of about 90° to just under about 120°. The arc length depends on the number of pleats (n). In the most basic configuration the arc length would be approximately 360/n, minus the distance require to provide for the formation of lobes 115 therebetween.

In some embodiments the arcs can also vary so that they have lengths different from each other and the radial angle between them can vary so that the distance between lobes can be controlled to bias their position about the balloon axis.

As the pleat forming surfaces push inwardly against the balloon 112, eventually the collective surfaces 72 will be in their fully reduced state, shown in FIG. 14. When in their fully reduced state, the pleat forming surfaces 72 define an almost complete circle, or substantially circular or elliptical, perimeter about the primary catheter shaft 10. In this reduced diameter state each pleat forming member 70 is separated, one from the other, by only a narrow portion of two opposing sections of balloon wall characterized as a 'stem' 114. In this state, lobes 115 of the balloon extend outward from a respective stem 114 and in between the pleat forming members 70 and into the housing space 58 now defined only by the compression members 80.

After the pleat forming members 70 have begun moving inward toward the balloon, or in some embodiments, after the pleat forming members are in their fully reduced state; the compression members 80 are actuated to move radially inward along their axis's to push against the lobes 115 of the balloon 110. Each compression member 80 includes a malleable compression surface 82 that contacts the underlying lobe 115.

At least one of the compression members 80 will press against the side branch balloon 122, and as a consequence the underlying lobe 115 of the primary balloon 112, as the compression members 80 are moved radially inward to the reduced state of FIG. 15. When the compression members 80 are fully reduced, the side branch balloon 122 will be essentially flattened or compressed against, and/or around, the lobe 115 against which it is positioned.

In some embodiments the compression surface 82 is constructed at least partially of an elastomeric material which is deformable against the material of the balloon. Some examples of suitable materials from which the compression surfaces can be constructed include, but are mot limited to: natural rubbers; silicone rubbers; foams; foam rubbers; synthetic rubbers including those based on polychloroprene, such as for example Neoprene; cellular urethanes, such as for example PORON®, from the Rogers Corporation; etc. In at least one embodiment, one or more of the compression surfaces comprise a composite layer of suitable materials to provide a variable durometer compression surface.

As shown, in some embodiments the pleat forming surfaces 72 define an arcuate surface, whereas each of the compression surfaces 82 are substantially linear or flat; at least initially. In some embodiments the compression surfaces 82 may have a shape other than substantially linear. Such shapes include curved or arced, such as in the manner of the pleat forming surfaces 72 described herein.

As the compression members 80 push against the lobes 115, the lobes acquire a substantially flattened shape (or other shape, depending on the actual shape of the compression surface and its malleability) on both their outside surface 116, where they are being compressed by the compression surface 82, and their inside surface 117, which is being pushed against and across the backside 74 of the adjacent pleat forming members 70. The compression surfaces 82 meanwhile are sufficiently malleable so as to not overly compress the lobes 115 against the comparatively harder surfaces of the pleat forming members 70, and will instead distort their otherwise linear surface around and against the lobes 115 to prevent rupture or other damage to the balloon.

In at least one embodiment the backside 74 of each pleat forming member 70 has a curved shape substantially the same as that of the pleat forming surface 72.

In some embodiments, the balloon 112 is heated to a temperature of between about 35° C. to about 75° C., during pleat formation and/or compression. Heating can be provided by conductive heating of one or more of the pleat forming members 70 and/or compression members 80; direct heating of the balloon from an external heat source; heating of the balloon inflation fluid; etc.

In some embodiments, as the balloon is being compressed by the compression members 80, the balloon 112 is evacuated. In some embodiments a vacuum is applied to the housing space 58 to further aid in the collapse of the lobes and to help the balloon attain its folded configuration such as in the manner previously described.

Figure 16:
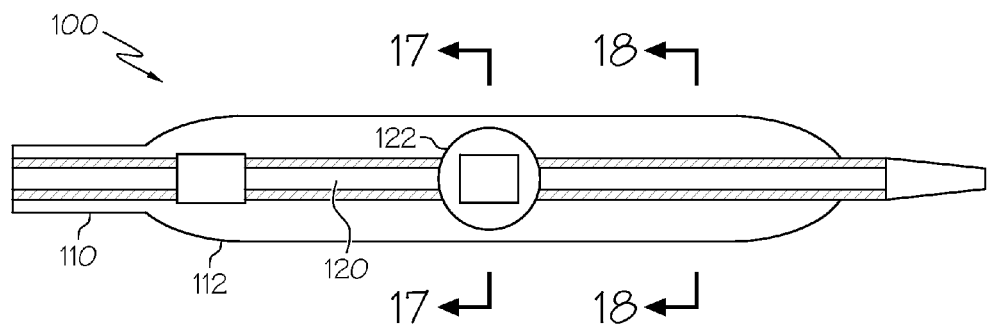
FIG. 16 is a longitudinal top-down view of a bifurcated balloon catheter following the folding and reduction of both the primary and side branch balloon in accordance with the operation depicted in FIGS. 13-25.
Figure 17:
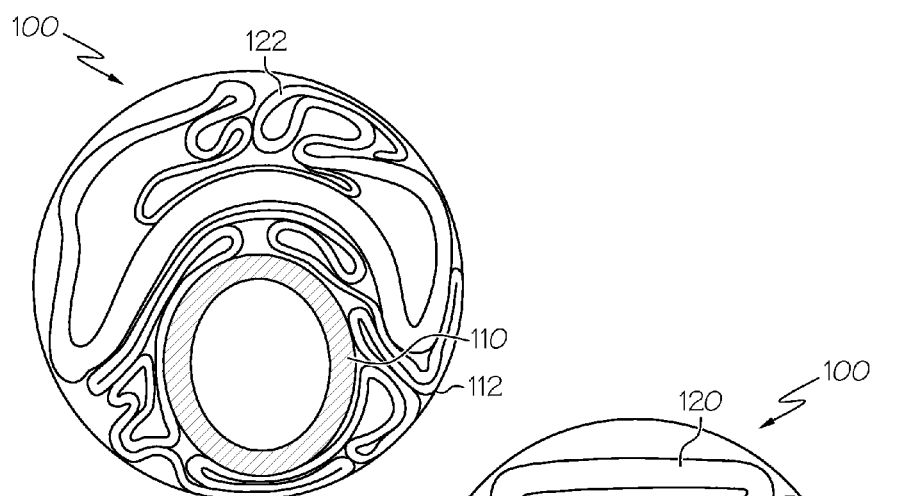
FIGS. 17 and 18 are cross-sectionals view of different portions of the bifurcated balloon catheter shown in FIG. 16.
Figure 18:
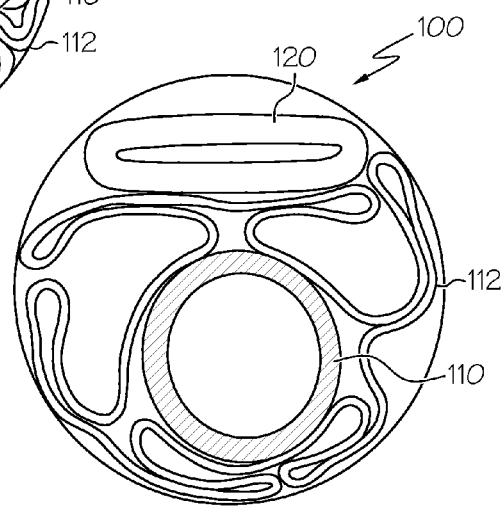

Once the balloon is in the fully reduced state, such as is depicted in FIG. 15, the compression members 80 and the pleat forming members 70 are actuated back to the open position and the folded balloon is removed from the housing 54. The resulting "T-fold" configuration of the primary balloon 112 is depicted in FIGS. 16-18.

The malleability of the compression members 80 to compress both the side branch balloon 122 and/or the primary balloon 112 simultaneously makes the present system suitable for use with any of a variety of bifurcated balloon catheters. In at least one embodiment for example a balloon catheter of the type having a "blister" balloon could be folded and reduced in a similar manner as the bifurcated catheter shown in FIGS. 13-15, where the "blister" takes the position of the side branch balloon 122 in the housing space. Examples of blister balloons of the type described are found in U.S. Published Application 2002/0193873; and U.S. Pat. No. 7,220,275; the entire contents of each being incorporated herein by reference.

In some embodiments the primary and secondary catheter shafts 110 and 120 are inserted into the housing together in the manner described, even after the side branch balloon 122 has been reduced in the manner described in relation to FIGS. 2-12.

Figure 19:
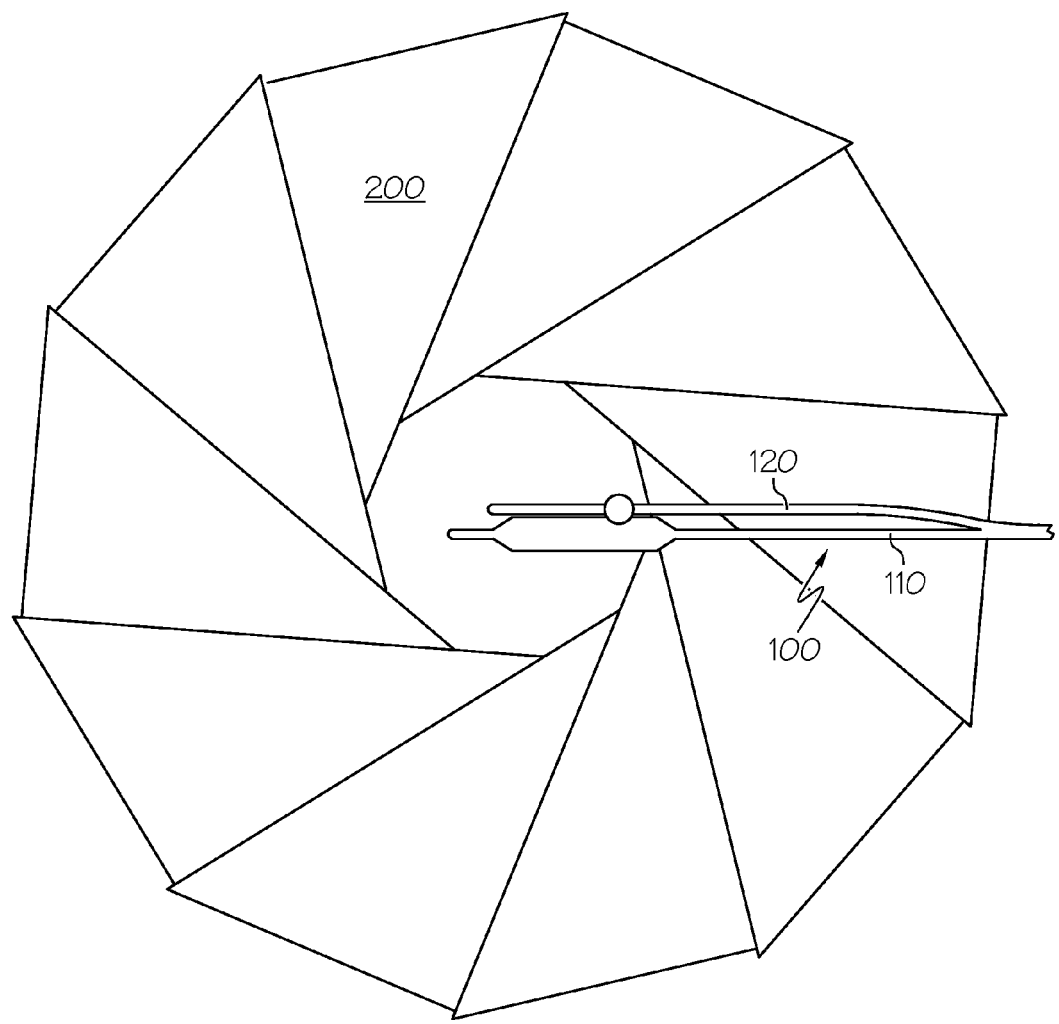
FIG. 19 is a front view of a catheter reducing iris.

Once the primary catheter shaft and the secondary catheter shaft are reduced and folded as described above, the distal portion of the catheter 100 is inserted into a reducing iris 200, such as is shown in FIG. 19 in order to heat set the entire catheter assembly 100. In some embodiments this final reduction and heat setting further reduces the catheter's balloons' profile.

The various systems and apparatuses described herein are suitable for use with any type of balloons made of any material. For example, balloons 112 and 122 may be constructed in whole or in part of both elastomeric and non-elastomeric materials.

Examples of non-elastomeric materials include, but are not limited to, polyolefins including polyethylene and polypropylene, polyesters, polyethers, polyamides, polyurethanes, polyimides, and so forth, as well as copolymers and terpolymers thereof. As used herein, the term "copolymer" shall hereinafter be used to refer to any polymer formed from two or more monomers.

Examples of suitable elastomeric materials include, but are not limited to, elastomeric block copolymers including the styrenic block copolymers such as styrene-ethylene/butylene-styrene (SEBS) block copolymers disclosed in U.S. Pat. No. 5,112,900 which is incorporated by reference herein in its entirety. Other suitable block copolymer elastomers include, but are not limited to, styrene-isoprene-styrene (SIS), styrene-butadiene-styrene (SBS), styrene-isobutylene-styrene (SIBS) and so forth. Block copolymer elastomers are also described in commonly assigned U.S. Pat. Nos. 6,406,457, 6,171,278, 6,146,356, 5,951,941, 5,830,182, 5,556,383, each of which is incorporated by reference herein in its entirety.

Elastomeric polyesters and copolyesters may be employed herein. Examples of elastomeric copolyesters include, but are not limited to, poly(ester-block ether) elastomers, poly(ester-block-ester) elastomers and so forth. Poly(ester-block-ether) elastomers are available under the tradename of HYTREL® from DuPont de Nemours & Co. and consist of hard segments of polybutylene terephthalate and soft segments based on long chain polyether glycols. These polymers are also available from DSM Engineering Plastics under the tradename of ARNITEL®.

Non-elastomeric polyesters and copolymers thereof may be employed such as the polyalkylene naphthalates including polyethylene terephthalate and polybutylene terephthalate, for example.

Polyamides including nylon, and copolymers thereof such as poly (ether-block-amides) available under the tradename of PEBAX® from Atofina Chemicals in Philadelphia, Pa., are suitable for use herein.

Suitable balloon materials are described in commonly assigned U.S. Pat. Nos. 5,549,552, 5,447,497, 5,348,538, 5,550,180, 5,403,340, 6,328,925, each of which is incorporated by reference herein in its entirety.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to."

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A balloon folding system for folding the balloons of a bifurcated balloon catheter, the system comprising:
   a catheter housing, the catheter housing constructed and arranged to removably receive at least a portion of a balloon catheter including a primary balloon and a side branch balloon, the catheter housing being defined by:
   at least three pleat forming members, the pleat forming members being distributed radially about a circumference of the catheter housing, each pleat forming member being movable between a radially open position and a radially closed position along a single axis, each pleat forming member having a pleat forming surface, the pleat forming surface constructed and arranged to engage an external surface of the primary balloon as each pleat forming member moves from the open to the closed position; and
   at least three compression members, the compression members being distributed radially about the circumference of the catheter housing and each compression member being positioned between two of the pleat forming members, each compression member being movable between a radially open position and a radially closed position along a single axis, each compression member having a compression surface,
   at least one compression surface constructed and arranged to engage an external surface of the side branch balloon, at least two compression surfaces constructed and arranged to engage an external surface of the primary balloon only after the pleat forming members begin moving from their radially open position to their radially closed position;
   the balloon folding system further comprising a side branch balloon reducing assembly comprising a die defining a side branch balloon reduction chamber, a pin and an actuation mechanism engaged to the pin, said reduction chamber having a substantially cylindrical shape and an open top, said pin having a substantially cylindrical shape.

2. The system of claim 1 wherein the pleat forming surface defines an arc.

3. The system of claim 2 wherein the arc measures less than 120 degrees.

4. The system of claim 2 wherein the compression surface is constructed of an elastomeric material.

5. A system for reducing a side branch balloon and for folding a primary balloon of a bifurcated balloon catheter, the system comprising:
   a primary housing, the primary housing constructed and arranged to removably receive and reduce the primary balloon into a folded and wrapped reduced diameter configuration; and
   a side branch reducing assembly, the assembly comprising:
   a die, the die defining at least one balloon reduction chamber, at least a portion of the at least one balloon reduction chamber having a substantially cylindrical shape and an open top;
   at least one pin, each pin having a substantially cylindrical shape, corresponding to the shape of the at least one balloon reduction chamber, such that each pin is constructed and arranged to be removably received into a corresponding balloon reduction chamber;
   an actuation mechanism, the actuation mechanism engaged to the at least one pin, the actuation mechanism moving the at least one pin between a position external to the at least one balloon reduction chamber and a position wherein the at least one pin is inserted into the at least one balloon reduction chamber through the open top.

6. The system of claim 5 wherein the die further defines a vacuum chamber, the vacuum chamber being in fluid communication with the at least one balloon reduction chamber.

7. The system of claim 5 wherein at least one of the catheter housing and the assembly being in communication with a heat source, the heat source applying heat to at least one of the primary balloon and the side branch balloon with heat to a temperature of about 35.degree. C. to about 75.degree. C.

8. The system of claim 5 wherein the catheter housing is disposed about a primary axis and the assembly is disposed about a secondary axis, the secondary axis forming an angle with the primary axis.

9. The system of claim 8 wherein the angle is about 90 degrees.

10. An assembly for reducing a side branch balloon of a side branch catheter shaft, the assembly comprising:
    a die, the die defining at least one balloon reduction chamber, at least a portion of the at least one balloon reduction chamber having a substantially cylindrical shape and an open top;
    at least one pin, each pin having a substantially cylindrical shape, corresponding to the shape of the at least one balloon reduction chamber, such that each pin is constructed and arranged to be removably received into a corresponding balloon reduction chamber;
    an actuation mechanism, the actuation mechanism engaged to the at least one pin, the actuation mechanism moving the at least one pin along an actuation axis between a position external to the at least one balloon reduction chamber and a position wherein the at least one pin is inserted into the at least one balloon reduction chamber through the open top;
    wherein said actuation axis is parallel to a central axis of the substantially cylindrical shape of the chamber.

11. The assembly of claim 10, comprising a plurality of pins, said die comprising a plurality of balloon reduction chambers, wherein each pin is engaged to said actuation mechanism.

* * * * *

UNITED STATES PATENT AND TRADEMARK OFFICE
CERTIFICATE OF CORRECTION

| | | |
|---|---|---|
| PATENT NO. | : 7,942,661 B2 | Page 1 of 1 |
| APPLICATION NO. | : 11/779485 | |
| DATED | : May 17, 2011 | |
| INVENTOR(S) | : Wang et al. | |

It is certified that error appears in the above-identified patent and that said Letters Patent is hereby corrected as shown below:

On the title page, item (75), 4th Line, delete "Stefen" and insert --Stefan--.

Signed and Sealed this
Seventeenth Day of January, 2012

David J. Kappos
*Director of the United States Patent and Trademark Office*